United States Patent
Black et al.

(10) Patent No.: US 6,727,399 B1
(45) Date of Patent: Apr. 27, 2004

(54) PROCESS FOR SEPARATING LINEAR ALPHA OLEFINS FROM SATURATED HYDROCARBONS

(75) Inventors: Jesse Raymond Black, Katy, TX (US); Laurent Fenouil, East Twickenham (GB)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/325,354

(22) Filed: Dec. 19, 2002

(51) Int. Cl.[7] .............................. C07C 7/00; C07C 7/152
(52) U.S. Cl. ...................... 585/867; 585/804; 585/833; 585/865
(58) Field of Search ................................ 585/867, 809, 585/833, 865

(56) References Cited

U.S. PATENT DOCUMENTS

| 4,946,560 | A | 8/1990 | Slaugh et al. | 203/38 |
| 6,018,089 | A | 1/2000 | Slaugh et al. | 585/867 |
| 6,184,431 | B1 | 2/2001 | Slaugh et al. | 585/867 |
| 6,271,434 | B1 | 8/2001 | Slaugh et al. | 585/867 |

OTHER PUBLICATIONS

U.S. patent application Ser. No. 10/325,340, Slaugh et al., filed Dec. 19, 2002.

*Primary Examiner*—Thuan D. Dang
(74) *Attorney, Agent, or Firm*—Yukiko Iwata

(57) ABSTRACT

A process for separating linear alpha olefins from a feedstock containing linear alpha olefins, saturated hydrocarbons, internal olefins, branched olefins, and alcohols, in particular, from a Fisher-Tropsch stream is provided.

44 Claims, 1 Drawing Sheet

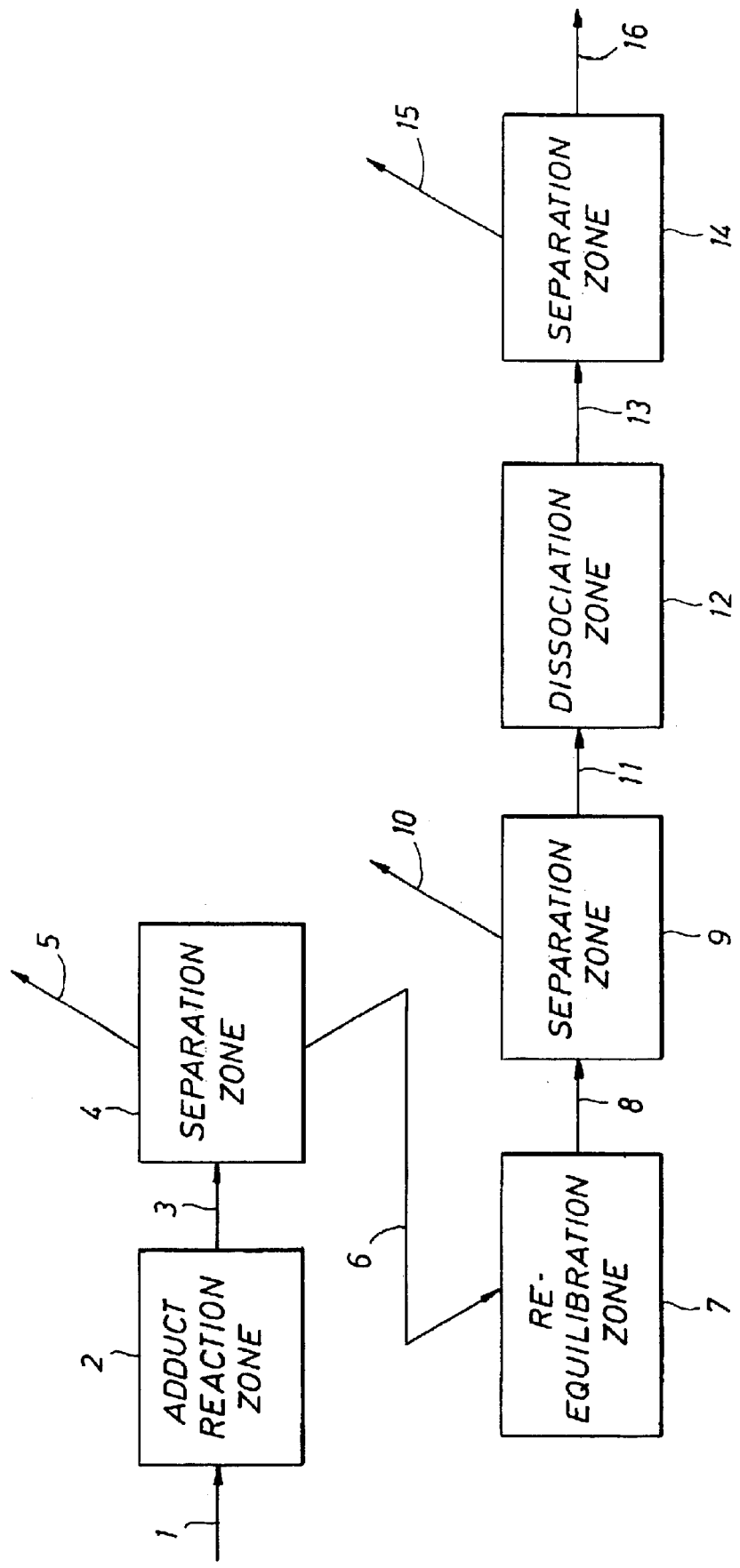

PROCESS FOR SEPARATING LINEAR ALPHA OLEFINS FROM SATURATED HYDROCARBONS

FIELD OF THE INVENTION

This invention relates to a process for separating linear alpha olefins from saturated hydrocarbons.

BACKGROUND OF THE INVENTION

Many industrial processes produce olefin/saturated hydrocarbon streams that are mixtures of olefins, saturated hydrocarbons, and oxygenates. Olefins are frequently used in the manufacture of polymers such as polyethylene, as drilling mud additives, or as intermediates for the production of oil additives and detergents. Some industrial processes manufacture olefins streams by oligomerizing ethylene over an alpha olefin catalyst to produce mixtures of alpha and internal olefins having a broad range of carbon numbers. However, these streams rely on the use of ethylene as a feedstock material, which add a significant cost to the manufacture of the olefin. On the other hand, the FT process starts with an inexpensive feedstock, syngas, generally derived from natural gas, coal, coke, and other carbonaceous compounds to make oligomers comprised of olefins, aromatics, saturates, and oxygenates.

The Fisher-Tropsch (FT) process, however, is not very selective to the production of olefins. While reaction conditions and catalysts can be tuned to manufacture a stream rich in the desired species within the FT product stream, a large percentage of the FT stream contains other types of compounds which must be separated from the olefins, which olefins are purified, and then sold into different markets. For example, a typical commercial FT stream will contain a mixture of saturated hydrocarbons, olefins, and oxygenates such as organic carboxylic acids, alcohols, ethers, esters, ketones, and aldehydes. All these compounds must be separated from the crude FT stream before a particular composition may be offered commercially. To further complicate the separation operation, the FT stream contains compounds having a wide spectrum of carbon numbers, as well as a wide variety of olefins, ranging from $C_2$–$C_{200}$ species, internal linear olefins, alpha linear olefins, internal branched olefins, alpha branched olefins, and cyclic olefins, many of which have similar molecular weights. Separating and isolating these species is no easy task. Conventional distillation methods are frequently inadequate to separate species having close boiling points.

Various processes have been proposed to efficiently separate the different species in a FT stream with sufficient purity that a particular composition is acceptable in the intended application.

It would be desirable to conduct a separation operation on a FT stream in which the activity and life of the separating agent is not diminished by the presence of impurities in the stream, such as oxygenates; which remains active under a wide band of average carbon numbers ranging from $C_5$–$C_{20}$, and which distinguishes between linear alpha olefins, branched alpha olefins, and paraffins in a FT stream.

U.S. Pat. No. 4,946,560 described a process for the separation of internal olefins from alpha olefins by carrying out a Diels-Alder reaction by contacting a feedstock with an adducting compound such as anthracene to form an olefin adduct (Diels-Alder adduct), separating the adduct from the feedstock, dissociating the olefin adduct through heat to produce anthracene and an olefin composition enriched in alpha olefin, and separating out the anthracene from the alpha olefin.

U.S. Pat. No. 6,184,431 describes a process for the separation of alpha and internal olefins from saturated compounds by contacting a feedstock with a linear polyaromatic compound to form a reaction mixture comprising linear polyaromatic compound-olefin adducts and saturated hydrocarbons, separating the adducts from the saturated hydrocarbons, then dissociating the linear polyaromatic compound-olefin adducts to form linear polyaromatic compounds and an olefin composition.

U.S. Pat. No. 6,271,434 describes a process for the separation of linear alpha olefins from a crude stream containing saturated hydrocarbons, internal olefins, branched olefins, and linear alpha olefins by contacting the feedstock with linear polyaromatic compound to form a reaction mixture comprising linear polyaromatic compound-olefin adducts, separating the adducts from the saturated hydrocarbons and dissociating the adducts to form linear polyaromatic compounds and olefin.

However, it is desirable to obtain a process with economical means to further separate the desired products.

SUMMARY OF THE INVENTION

There is provided a process for separating linear alpha olefins from a feedstock composition comprising linear alpha olefins, saturated hydrocarbons, internal olefins, branched olefins, and alcohol comprising:

a) contacting the feedstock composition with a linear polyaromatic compound under conditions effective to form a reaction mixture comprising linear polyaromatic compound-olefins adducts, saturated hydrocarbons, unreacted olefins, and alcohols and unreacted polyaromatic compound;

b) separating the linear polyaromatic compound-olefin adducts from the saturated hydrocarbons, unreacted olefins and alcohol in the reaction mixture to form a hydrocarbon stream comprising saturated hydrocarbons, unreacted olefins and alcohols and an adducted stream comprising the linear polyaromatic compound-olefin adducts and unreacted linear polyaromatic compound;

c) re-equilibrating the adducted stream by partially and selectively dissociating the linear polyaromatic compound-olefin adducts under conditions effective to increase the percentage of the polyaromatic compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound;

d) separating the linear polyaromatic compound-olefin adducts from the dissociated olefins in the equilibrated stream to form an olefin stream comprising dissociated olefins and a linear alpha-olefin adducted stream comprising the linear polyaromatic compound-olefin adducts and linear polyaromatic compound;

e) dissociating the linear polyaromatic compound-olefin adducts in the linear alpha olefin adducted stream to form linear polyaromatic compounds and alpha olefin enriched olefin product; and f) separating the alpha olefin enriched olefin product from the polyaromatic compound, whereby the alpha olefin enriched olefin product is enriched in the concentration of olefins over the concentration of olefins in the feedstock and enriched in the concentration of linear alpha olefins over other olefins in the feedstock.

Further, a process for separating linear alpha olefins from a Fisher-Tropsch feedstock having an average carbon number in the range of from 6 to 16 and having a predominant olefin species within said range, said feedstock comprising linear alpha olefins, olefins other than linear alpha olefins, saturated hydrocarbons, and alcohols comprising:

a) contacting said feedstock with a linear polyaromatic compound comprising anthracene or benzanthracene under conditions effective to form a reaction mixture comprising linear polyaromatic compound-olefin adducts, unreacted olefins, alcohols, saturated hydrocarbons, and unreacted polyaromatic compound;

b) separating the linear polyaromatic compound-olefin adducts from the saturated hydrocarbons, unreacted olefins and alcohol in the reaction mixture to form a hydrocarbon stream comprising saturated hydrocarbons, unreacted olefins, and alcohols, and an adducted stream comprising the linear polyaromatic compound-olefin adducts and unreacted linear polyaromatic compound;

c) re-equilibrating the adducted stream by partially and selectively dissociating the linear polyaromatic compound-olefin adducts under conditions effective to increase the percentage of the polyaromatic compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound;

d) separating the linear polyaromatic compound-olefin adducts from the dissociated olefins in the equilibrated stream to form an olefin stream comprising dissociated olefins and a linear alpha-olefin adducted stream comprising the linear polyaromatic compound-olefin adducts and linear polyaromatic compound;

e) dissociating the linear polyaromatic compound-olefin adducts in the linear alpha olefin adducted stream to form linear polyaromatic compounds and alpha olefin enriched olefin product; and f) separating the alpha olefin enriched olefin product from the polyaromatic compound, whereby the alpha olefin enriched olefin product is enriched in the concentration of olefins over the concentration of olefins in the feedstock and enriched in the concentration of linear alpha olefins over other olefins in the feedstock.

BRIEF DESCRIPTION OF THE DRAWINGS

The FIGURE is a block flow diagram representing the process of adducting, separating, re-equilibrating, separating, dissociating, and separating to provide linear alpha olefin composition.

DETAILED DESCRIPTION OF THE INVENTION

This invention relates to a process for separating and recovering alpha olefins from saturated hydrocarbons and alcohols, and in particular, to a process for separating and optionally recovering linear alpha olefins from saturated hydrocarbons in a FT stream.

It has been found that in a process such as described in U.S. Pat. No. 6,271,434, in order to obtain increased alpha olefin purity one would set up the process as A-D-C-A-D-C-Dfinal and so on wherein. A is adducting, D is distillation, and C is cracking or dissociation steps. It has been found that by using a re-equilibration step, R, a cracking step that can be quite complicated can be eliminated. Thus, simplifying the process to A-D-R-D-C-Dfinal.

The feed stream to be treated typically comprises olefins, saturated hydrocarbons, and alcohols. The class of saturated hydrocarbons as used herein includes at least a paraffin. The class of saturated hydrocarbons may also include other molecules such as cycloparaffins.

An olefin means any compound containing at least one carbon-carbon double bond. The olefins may be linear, branched, conjugated, contain multiple double bonds anywhere along the chain, substituted, unsubstituted, contain aryl or alicyclic groups, or contain heteroatoms.

The olefins may contain aryl moieties along with an aliphatic or cycloaliphatic moiety within the same compound, or may consist solely of an aliphatic, cycloaliphatic, or cycloaliphatic with aliphatic moieties on the compound. Preferably, the olefin is an aliphatic compound.

The olefin may be branched or linear. Examples of branching include alkyl, aryl, or alicyclic branches. The number of unsaturation points along the chain is also not limited. The olefin may be a mono-, di-, tri-, etc. unsaturated olefin, optionally conjugated. The olefin may also contain acetylenic unsaturation.

An alpha olefin is an olefin whose double bond is located on both of $\alpha$ and $\beta$ carbon atoms. An $\alpha$ carbon atom is any terminal carbon atom, regardless of how long the chain is relative to other chain lengths in a molecule. The alpha olefin may be linear or branched. Branches or functional groups may be located on double bond carbon atoms, on carbon atoms adjacent to the double bond carbon atoms, or anywhere else along the carbon backbone. The alpha olefin may also be a poly-ene, wherein two or more points of unsaturation may be located anywhere along the molecule, so long as at least on double bond is in the alpha position.

An internal olefin(s) is an olefin whose double bond is located anywhere along the carbon chain except at any terminal carbon atom. The internal olefin may be linear or branched. The location of a branch or substitution on the internal olefin is not limited. Branches or functional groups may be located on the double bond carbon atoms, on carbon atoms adjacent to the double bond carbon atoms, or anywhere else along the carbon backbone.

The olefin may also be substituted with chemically reactive functional groups. Examples of chemically reactive functional groups are carboxyl, aldehyde, keto, thio, ether, hydroxyl, and amine. The number of functional groups on a molecule is not limited. The functional groups may be located anywhere along the carbon backbone.

The feedstock can be produced by commercial processes such as the oligomerization of ethylene, optionally followed by isomerization and disproportionation. Alternatively, the feedstock may be produced by the Fisher-Tropsch process, which typically contains a high proportion of paraffins. A Fisher-Tropsch process catalytically hydrogenates CO to produce compositions containing aliphatic molecular chains. Other processes for making feedstocks which may contain mixtures of olefins and paraffins include the dehydrogenation of paraffin, such as those made by the Pacol™ processes of UOP, and the cracking of waxes. The most preferred feedstock is that obtained from a Fisher-Tropsch (FT) synthesis.

FT catalysts and reaction conditions can be selected to provide a particular mix of species in the reaction product stream. For example, the particular catalyst and reaction conditions may be tuned to enhance the amount of olefins and decrease the amount of paraffins and oxygenates in the stream. Alternatively, the catalyst and reaction conditions may be tuned to enhance the amount of paraffins and decrease the amount of olefins and oxygenates in the stream.

Generally, the reaction conditions will vary depending on the type of equipment employed. The FT reaction temperatures vary between 100° C. to 500° C., an inlet gas pressure to the reactor from atmospheric to 1500 psig, and an $H_2/CO$ ratio from 0.5:1 to 5:1, preferably from 1.8:1 to 2.2:1, and gas hourly space velocity ranging from 1 to 10,000 v/v/hour. A variety of reactor vessel configurations can be used, including a fluidized(entrained) bed, a fixed bed, and a slurried bed. The temperature in these beds can be adjusted by those of ordinary skill to optimize the formation of FT products, including hydrocarbons, and particularly, olefins and types of olefins. To illustrate without limitation, in fluidized (entrained) bed(s), the temperature of reaction is generally high- e.g. ranging from 280° to 350° C., preferably 310° to 340° C. If a fixed bed reactor(s) is used, the reaction temperature is generally ranges within 200° C. to 256° C., preferably between 210° and 240° C., and when a slurry bed reactor(s) is used, the temperature is generally within the range of 190° C. to 270° C.

The catalyst used in the FT process is any known in the art, but preferably from among Mo, W, and Group VIII compounds, including iron, cobalt, ruthenium, rhodium, platinum, palladium, iridium, osmium, combinations of the foregoing, combinations with other metals, and each being in the free metal form or as alloys, or as an oxide or carbide or other compound, or as a salt. The catalysts may also contain promoters to promote the catalyst's activity, stability, or selectivity. Suitable promoters include alkali or alkaline earth metals, in free or combined form as an oxide, hydroxide, salt, or combinations thereof. Suitable catalysts are described for example in U.S. Pat. Nos. 6,271,434 and 6,184,431 which disclosures are hereby incorporated by reference.

An FT stream generally contains virtually no sulfur or nitrogen compounds, which may be deleterious to other catalysts which derivatize the olefins or catalyze the reaction of olefins in other oligomerization or polymerization processes. Regardless of the method used, however, the FT process is not very selective to a particular species, and yields a wide variety of species within a composition.

Examples of some of the species found in any FT stream include paraffins having a broad spectrum of molecular weights, alcohols, acids, ketones, and aldehydes, and small amounts of aromatics. The linear polyaromatic compound used in the process of the invention, however, is particularly well adapted for the separation of olefins from saturated hydrocarbons in an FT stream in the presence of oxygenates since oxygenates do not significantly impair the performance of the linear polyaromatic compound.

While reference is made to a FT stream, it is to be understood that any stream made by any process containing olefins and saturated hydrocarbons are suitable feedstocks for the process of the invention. Most crude FT streams contain from 5% to 99% olefins, the remainder being saturated hydrocarbons comprising paraffins and cycloparaffins, and optionally other compounds such as aromatics optionally containing saturated or unsaturated alkyl branches, and oxygenates, based on the weight of all ingredients in the feedstock stream to the process of the invention. The preferred amount of olefin present in the FT stream ranges from 15 wt. % to 70 wt. %. The amount of linear alpha olefin in the FT stream is not limited, but preferably ranges from 15 wt. % to 60 wt. %. The amount of other olefins, including branched olefins and internal olefins, both linear and branched, is also not limited, but preferably ranges from 1 wt. % to 55 wt. %, more typically from 5 wt. % to 45 wt. %. The amount of paraffin in most FT streams range from 5 wt. % to 99 wt. %. In some FT streams, the FT catalyst is tuned to enhance the olefin concentration and decrease the paraffin concentration. In these streams, the amount of paraffin generally ranges from 5 to 65 wt. % of the stream. In other FT streams where the FT catalyst is tuned to enhance the amount of paraffin, the amount of paraffin in the stream ranges from 65 wt. % to 99 wt. %. The amounts of other compounds in a FT stream, such as oxygenates and aromatics, make up most of the remainder of the FT stream, and are generally present in amounts ranging from 5 wt. % to 30 wt. %. Minor amounts of other by-products and impurities, less than 5 wt. %, may be present in most FT streams. An FT stream which consists essentially of paraffins, olefins, aromatics and oxygenates can include such minor amounts of other by-products and impurities.

The feedstock may be a processed FT stream which has been fractionated and/or purified by a conventional distillation, extraction, or other separation methods to remove some of the paraffins, high and low molecular weight species, and oxygenates from the crude stream. When the separation operation is conducted by distilling the reaction mixture containing the adduct, it is preferred that the feedstock used in the process of the invention contain an average carbon number ranging from $C_5-C_{20}$ and wherein the predominant olefin species in the feedstock is within the range of $C_5-C_{20}$, inclusive.

The polyaromatic adducting compound efficiently separates the saturated hydrocarbons and alcohols from the olefins when the average carbon number of the feedstock and the predominant olefinic species is within this range, inclusive, by the formation of the Diels-Alder adduct. When the average carbon number of the feedstock exceeds $C_{20}$, the polyaromatic compound-olefin adduct boils at a lower temperature than many of the species in the $C_{20}$ + feedstock composition, thereby leaving these high boiling species in the reaction mixture bottoms containing the adduct.

Accordingly, the particular polyaromatic compound and the particular feedstock composition should be so selected that the polyaromatic compound-olefin adduct composition in the reaction mixture boils at a higher temperature than the amount of unreacted paraffin species in the feedstock one desires to separate. Therefore, in this preferred embodiment, the feedstock stream is one which contains an average carbon number in the range from 5 to 20, and more preferably in the range from 6 to 16, and wherein the predominant olefin species is within these ranges, inclusive. These types of FT streams are generally processed by one of the techniques identified above to substantially remove cuts containing ingredients below or exceeding the range of $C_5-C_{20}$.

In the event that one desires to employ a feedstock outside of the range having an average carbon number of from 5 to 20, other separation techniques can be used to separate the adduct from the unreacted reaction mixture, including the selection of higher boiling polyaromatic compounds and/or other separation techniques such as liquid/liquid extraction or crystallization. These techniques, of course, can also be used with feedstocks having average carbon number in the range of 5 to 20, inclusive.

The linear polyaromatic compound is utilized in the instant process to form the adduct with the olefins in the feed stream. As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain so long as at least three fused rings are present in a linear arrangement; as well as those containing a heteroatom which do not interfere in the separation of olefins from saturated hydrocarbons.

The linear polyaromatic compound has a preferential selectivity toward adducting with linear alpha olefin compounds, and secondly with other olefins, and last with paraffins, with which the compound is virtually unreactive under any operating condition outside of cracking conditions. The linear polyaromatic compound of choice is one which has a selectivity for linear alpha olefin compounds over other olefins greater than 1:1 by mole, preferably 2:1 or more, more preferably 4:1.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and not so large as to block the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

The process of the instant invention is basically at least a six step process wherein (a) a linear polyaromatic compound is reacted with a feedstock comprising saturated hydrocarbons and various olefins including linear alpha olefins, branched olefins, and internal olefins, to form an adduct of an olefin-linear polyaromatic compound, (b) the adduct is separated from the reaction mixture, typically by flashing or distilling the unreacted components including saturated hydrocarbons and alcohols at the overhead and recovering the adduct as part of a bottoms stream, (c) the stream containing the adduct is subjected to re-equilibration under conditions effective to re-equilibrating the adducted stream by partially and selectively dissociating the linear polyaromatic compound-olefin adducts under conditions effective to increase the percentage of the polyaromatic compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound, (d) the polyaromatic compound-olefin adducts from step (c) is separated from the re-equilibrated mixture; (e) the polyaromatic compound-olefin adducts separated in step (d) is dissociated to release the olefins and regenerate the linear polyaromatic compound; and (f) the olefins enriched in alpha olefin is separated from the polyaromatic compound The olefins stream from step (d) can be optionally recycled into the feedstock of step (a). The unreacted and dissociated polyaromatic compound can be recycled into the feedstock of step (a).

The Diels-Alder adduct forming reaction is carried out in a conventional fashion and reaction zone. An example of a preferred adduct reaction zone is a plug flow reactor operated in a upflow mode, wherein both the linear polyaromatic compound and the feedstock is mixed and fed into the bottom of the plug flow reactor continuously. The reaction products are continuously withdrawn from the top of the reactor.

Another example of a suitable adduct reaction zone is a continuously stirred tank reactor(s), configured as a single unit, in parallel, or in series, wherein olefin and linear polyaromatic compound are added continuously to a stirred tank(s) to form a liquid reaction mixture, and the reaction mixture is continuously withdrawn from the stirred tank(s).

For lower boiling feedstocks (lighter feedstock), a bubble column may be preferred as the adduct reaction zone. Alternatively, the reaction may be carried out in a batch reactor.

The adducting reaction is typically carried out at a temperature in the range where the linear polyaromatic compound is in a liquid form. Suitably preferred temperatures are in the range of from about 200, preferably from about 220° C., most preferably from about 240° C., to about 290° C., preferably to about 280° C., and most preferably to about 265° C. Operating pressures are not critical and set to ensure that none of the olefin stream vaporizes. This pressure will depend on the olefin feedstock used. A typical operating pressure could from about 50 psig ( 4.5 kg/m$^2$) to about 200 psig (15 kg/m$^2$). The reaction can be carried out in the gas phase under vacuum or liquid phase or mixed gas-liquid phase, depending on the volatility of the feedstock, but generally in the liquid phase.

Stoichiometric ratios or an excess of either olefin or linear polyaromatic compound can be used to form the adducts. The molar ratio of olefin to linear polyaromatic compound is preferably from 0.1:1 up to 10:1. Preferably, a molar excess of linear polyaromatic compound is used to ensure a complete and large recovery of all olefins in the adduction zone, step (a). When a greater selectivity toward forming adducts with linear alpha olefins are desired in the adduction zone, the molar ratio of linear polyaromatic compounds to olefins may be moderated, for example, desirably closer towards a 0.5:1 to 1.5:1 molar ratio. The residence time is for a time sufficient to adduct the desired amount of linear polyaromatic compound with the olefin. Typical reaction times range from 30 minutes to 4 hours in a batch reaction.

An inert solvent can be utilized to dissolve the feedstock olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. Preferably, the solvent should be a hydrocarbon having 20 carbon atoms or less. The amount of solvent to be employed can vary over a wide range without a deleterious effect on the reaction.

In one embodiment of the invention, however, the feedstock adduction, and particularly, the linear polyaromatic compound-olefin adduct formation is carried out in the absence of a solvent to improve the rate of reaction and avoid additional equipment and process steps for separating the solvent.

After the linear polyaromatic compound-olefin adduct has been formed, the reaction mixture flows to a separation vessel effective for separating the saturated hydrocarbons from the linear polyaromatic compound-olefin adduct to form a saturated hydrocarbon stream and an olefin adducted stream. Due to the large molecular weight and structural difference between the linear polyaromatic compound-olefin adduct and the saturated hydrocarbons in the reaction mixture, conventional separation techniques are quite suitable for removing the unreacted saturated hydrocarbons. For example, the non-adducted compounds may be removed overhead or in fractions by vacuum or flash distillation of the reaction mixture to leave the linear polyaromatic compound-olefin adduct and unreacted linear polyaromatic compound as a liquid bottoms. The non-adducted compounds which are removed include the saturated hydrocarbons, the aromatics, and the oxygenates such as the alcohols, ketones, acids, along with internal and branched olefins which did not form an adduct with the linear polyaromatic compound.

Alternatively, the linear polyaromatic compound-olefin adduct is separated by cooling the reaction mixture until the adduct crystallizes out, followed by filtration or centrifugation to remove the unreacted olefin.

In most cases, any unreacted linear polyaromatic compound will separate out with the linear polyaromatic compound-olefin adduct in the adducted olefin stream. Other ingredients, such as small amounts of higher molecular weight unreacted olefins, internal olefins, and branched olefins, may remain in the adducted olefin stream.

The improvement consists of adding a re-equilibration reaction zone which can preferably be carried out using a second reactor after the distillation step which removes alkanes, unreacted olefins, and miscellaneous compounds from the adduct reaction product. This re-equilibration reactor (or re-equilibrator) can be a plug flow reactor, CSTR, series of CSTR's, batch reactor, liquid downflow bubble column reactor operated in the liquid phase and at temperatures intermediate between the adduct zone (adduct-forming reactor) and the dissociation zone (adduct-cracking reactor). This reactor may preferably operate at a temperature in the range of from about 280° C. to about 310° C. The re-equilibrium reaction is preferably carried out at a higher temperature than the adducting reaction. The residence time within a re-equilibrator should be sufficiently long to allow the adducted stream within the re-equilibrator to reach the equilibrium as described below. The residence time within the re-equilibrator will generally run from 30 minutes to 6 hours.

The purpose of this re-equilibration reactor is to allow adducts, polyaromatic compound (e.g., anthracene), and olefins to approach a new equilibrium where some of the adduct has cracked back (dissociated) to olefin and polyaromatic compound. Relatively more of the internal olefin adducts cracks than the α-olefin effectively providing a α-olefin selectivity increase. Also, higher reaction temperature takes advantage of the thermodynamics of adduct formation. The equilibrium constant for the internal olefins decreases faster with increasing temperature than does the equilibrium constant for the α-olefin, thus providing an incremental selectivity improvement.

After this re-equilibration, the dissociated or released olefins are removed by one or more separation steps such as distillation or crystallization. For example, the released olefins may be removed at the overhead or in fractions by vacuum or flash distillation of the reaction mixture to leave the linear polyaromatic compound-olefin adduct and unreacted or dissociated linear polyaromatic compound as a liquid bottoms.

Adding the re-equilibrator can eliminate one dissociation step and simplifies overall plant design compared to a combination of two adduct formation cycles to provide the desired linear alpha olefin composition. Typically, α-olefin content in the product is increased by 3+ mole %.

The next step of the instant process is to dissociate the linear polyaromatic compound-linear alpha olefin adduct. The dissociation process can be accomplished by feeding the adducted linear alpha olefin stream to a dissociation vessel where the adducted olefins stream is heated or pyrolyzed at a temperature effective to dissociate the adduct, typically from about 250° to about 500° C., preferably from about 300° to about 350° C. This pyrolysis frees the olefins from the linear polyaromatic compound. Typically, the majority of the adduct is dissociated. Preferably the adduct is substantially dissociated, i.e., at least 90% by mole, more preferably at least 95% by mole. The remainder of the adduct is removed with the polyaromatic compounds during separation and can be recycled to the adduct reactor. The linear polyaromatic compound is then separated from the resulting mixture by any conventional means, which may occur simultaneously with the pyrolysis operation, such as by vacuum or flash distilling off the olefins along with any impurities at the pyrolysis temperatures, and removing the linear polyaromatic compound as a bottoms from the adduct dissociation zone. Other separation techniques include filtration and centrifugation.

The linear polyaromatic compound may be recycled back to the adduct reaction zone. The separated olefin composition is now enriched in linear alpha olefin concentration over that of the feedstock to the adduct reaction zone, and the concentration of saturated hydrocarbons and branched olefins in the olefin composition is reduced over that of the feedstock. Likewise, when the saturated hydrocarbons are separated from the linear polyaromatic compound-olefin adduct in the separation vessel as a saturated hydrocarbon stream, the saturated hydrocarbon stream is enriched in its concentration of saturated hydrocarbon over the concentration of saturated hydrocarbon in the feedstock to the adduct reaction zone. Each of the olefin composition and the saturated hydrocarbon stream may be recovered and isolated for use into other applications or as intermediates in other reactive processes.

With reference to the Figure, feedstock 1, is provided to an adduct reaction zone 2, whereby the feedstock is contacted with a linear polyaromatic compound thereby producing a reaction mixture 3 comprising linear polyaromatic compound-olefins adducts, saturated hydrocarbons, unreacted olefins, alcohols and unreacted linear polyaromatic compound. The reaction mixture is separated in the separation zone 4 to a hydrocarbon stream 5 comprising saturated hydrocarbons, unreacted olefins and alcohols and an adducted stream 6 comprising the linear polyaromatic compound-olefin adducts and unreacted linear polyaromatic compound. The adducted stream is provided to an re-equilibration zone 7, whereby the adducted stream is heated to the equilibration temperature thereby producing a re-equilibrated stream 8 comprising linear polyaromatic compound-olefin adducts, dissociated olefins, and unreacted linear polyaromatic compound and dissociated linear polyaromatic compound. The equilibration is carried out at a temperature effective to increase the percentage of the polyaromatic compound reacted with linear alpha olefins over all other olefins reacted with the polyaromatic compound in the stream. The re-equilibrated stream is separated in the separation zone 9 to an olefin stream 10 comprising the dissociated olefins and a linear alpha-olefin adducted stream 11 comprising the polyaromatic compound-olefin adducts and unreacted and dissociated linear polyaromatic compound. The polyaromatic compound-olefin adducts are dissociated (or cracked) in the dissociation zone 12 to form linear polyaromatic compounds and linear alpha-olefin-enriched olefin product thereby producing a dissociated stream 13. The alpha-olefin-enriched olefin product is separated in the separation zone 14 to the polyaromatic compound 15 and alpha-olefin-enriched olefin product 16.

For the purpose of determining whether a species is enriched or reduced by the process, consider the concentration of the species in the feedstock and in the product stream. If the concentration of the species in the feedstock is higher than its concentration in the product, then the process reduces the species. If the concentration of the species in the product stream is higher than its concentration in the feedstock, then the process enriches the species. For the purpose of determining whether a set of species is enriched or reduced by the process, consider the sum of the concentrations of the set of the species in the feedstock and product stream. If the sum of the concentrations of the set of species in the feedstock is higher than the sum of their concentrations in the product, then the process reduces the set of species. If the sum of the concentrations of the set of species in the product stream is higher than the sum of their concentrations in the feedstock, then the process enriches the set of species.

When a species (set of species) is reduced by the process the percentage reduction of the species (set of species) is calculated by subtracting the concentration of the species (sum of concentrations of the set of species) in the product stream from the concentration of the species (sum of concentrations of the set of species) in the feedstock, then dividing this difference by the concentration of the species (sum of concentrations of the set of species) in the feedstock, and then multiplying by 100. When a species (set of species) is enriched by the process the percentage enrichment of the species (set of species) is calculated by subtracting the concentration of the species (sum of concentrations of the set of species) in the feedstock from the concentration of the species (sum of concentrations of the set of species) in the product stream, then dividing this difference by the concentration of the species (sum of concentrations of the set of species) in the feedstock, and then multiplying by 100.

For example, consider that a feedstock contains 40% hexane, while the product stream of the process contains only 5% hexane. Thus hexane is reduced by the process. The percentage of hexane reduction is given as $(( 40-5)/40) \times 100 = 87.5\%$.

For example, consider that a feedstock contains 35% 1-decene and 5% 2-decene, while the product stream contains 90% 1-decene and 2% 2-decene. Considering only 1-decene, 1-decene is enriched by the process. The percentage enrichment of 1-decene is given as $(( 90-35)/35) \times 100 = 157.1\%$. Considering only 2-decene, 2-decene is reduced by the process. The percentage reduction of 2-decene is given by $((5-2)/5) \times 100 = 60\%$. Considering the set of olefins (i.e., 1-decene and 2-decene), the set of olefins is enriched by the process. The percentage enrichment of the set of olefins is given by $((90+2)-(35+5))/(35+5)) \times 100 = 130\%$.

Another measure of enrichment or reduction by the process is the enrichment or reduction of a subset of a set of species relative to the set of species. For the purpose of determining whether a subset of set of species is enriched or reduced by the process, consider the sum of concentrations of the subset in the feedstock and in the product stream. If the sum of concentrations of the subset in the feedstock is higher than the sum of concentrations of the subset in the product, then the process reduces the subset of the set of species. If the sum of the concentrations of the subset in the product stream is higher than the sum of the concentrations of the subset in the feedstock, then the process enriches the subset of set of species.

Two measures of reduction or enrichment of a subset of a set of species can be used. For reduction, the first measure is calculated by a two-step procedure. Divide the sum of the concentrations of the subset in the feedstock by the sum of concentrations of the set of species in the feedstock, then multiply 100. Call this X%. Divide the sum of the concentrations of the subset in the product stream by the sum of concentrations of the set of species in the product stream, then multiply by 100. Call this Y%. The subset relative to the set is then said to be reduced from X% to Y% where Y is less than X. For reduction, the second measure is derived from the first measure by subtracting Y% from X%, then dividing this difference by X%, then multiplying by 100. This is called the percentage reduction of the subset relative to the set of species. For enrichment, the first measure is calculated by a two-step procedure. Divide the sum of the concentrations of the subset in the feedstock by the sum of concentrations of the set of species in the feedstock, then multiply by 100. Call this X%. Divide the sum of the concentrations of the subset in the product stream by the sum of concentrations of the set of species in the product stream, then multiply by 100. Call this Y%. The subset relative to the set is then said to be enriched from X% to Y% where Y is greater than X. For enrichment, the second measure is derived from the first measure by subtracting X% from Y%, then dividing this difference by X%, then multiplying by 100. This is called the percentage enrichment of the subset relative to the set of species.

For example, consider that a feedstock contains 35% 1-decene and 5% 2-decene, while the product stream contains 90% 1-decene and 2% 2-decene. Consider 1-decene and 2-decene to be the set of species. Consider 1-decene to be the subset. The subset 1-decene is enriched relative to the set of species because its concentration is higher in the product. The percentage of subset 1-decene in the set 1-decene and 2-decene in the product (Y%) is $90/(90+2) = 97.83\%$. The percentage of subset 1-decene in the feedstock (X%) is $35/(35+5) = 87.5\%$. Thus, 1-decene is enriched from 87.5% to 97.83% in the set of species. The percentage enrichment of 1-decene relative to 1-decene and 2-decene is given by ((97.83−87.5)/87.5)×100=118.5%. Now consider 2-decene to be the subset. The subset 2-decene is reduced relative to the set of species because its concentration is lower in the product. The percentage of subset 2-decene in the product is 2/(90+2)×100=2.17%. The percentage of subset 2-decene in the feedstock is 5/(35+5)×100=12.5%. Thus 2-decene is reduced from 12.5% to 2.17% in the set of species. The percentage reduction of 2-decene relative to 1-decene and 2-decene is given by ((12.5−2.17)/12.5)×100= 816%

The process of the invention will enrich the total concentration of linear alpha olefins, and reduce the concentration of saturated hydrocarbons and other olefins such as branched olefins and internal olefins compared to their respective concentrations in the feedstock.

In one embodiment, the concentration of all olefins in the saturated hydrocarbon stream are reduced through the process of the invention in only one pass by at least 15%, preferably at least 30%, more preferably at least 50%, over the concentration of all the olefins in the feedstock. In another embodiment, the concentration of linear alpha olefins in the saturated hydrocarbon stream are reduced in one pass by at least 30%, more preferably by at least 40%, most preferably by at least 60%, over the concentration of linear alpha olefins present in the feedstock stream.

The amount of excess linear polyaromatic compound present in the adducting reaction zone, the residence time, and temperature, will affect the amount of internal or branched olefins adducting with the linear polyaromatic compound, and therefore, the amount of internal or branched olefins left unreacted and passing into the saturated hydrocarbon stream. While the linear polyaromatic compound preferentially adducts with a linear alpha olefin, the presence of a large excess of the polyaromatic compound relative to the amount of linear alpha olefins present in the feedstock coupled with long residence times, will leave un-adducted linear polyaromatic compounds free to adduct with the internal and branched olefins, thereby enhancing the reduction of these olefins in the saturated hydrocarbon stream over the concentration of these olefins in the feedstock stream. In another embodiment, the concentration of internal olefins present in the saturated hydrocarbon stream is reduced by from 1 to 50% over the concentration of linear internal olefins present in the feedstock.

In another embodiment of the invention, the concentration of saturated hydrocarbons in the alpha olefin enriched olefin product is reduced through the process of the invention in only one pass by at least 80%, preferably by at least 90%, more preferably by at least 95% over the concentration of saturated hydrocarbon in the feedstock, and most preferably by 100%.

As above, the percentage reduction or enrichment of branched olefins and internal olefins in the olefin composition depends upon the amount of linear polyaromatic compound, temperature, and residence time of the feedstock in the adducting reaction zone. In one embodiment, the concentration of branched olefins in the olefin composition is reduced over the concentration of branched olefins in the feedstock.

In the invention, the concentration of linear alpha olefins in the olefin composition is enriched over the concentration of linear alpha olefins present in the feedstock stream. In an embodiment of the invention, the concentration of linear alpha olefins present in the olefin composition is enriched by at least 100%, more preferably by at least 140%, most preferably by at least 155%, over the concentration of linear alpha olefins present in the feedstock composition. The concentration of linear alpha olefins after the separation step (f) is at least 90%, preferably at least 95%, more preferably at least 96% by weight of the total olefin concentration.

In another embodiment, the concentration of all olefins in the olefin composition is enriched over the concentration of all olefins in the feedstock stream. The degree of olefin enrichment varies inversely with the concentration of olefins present in the feedstock. In a preferred aspect of this embodiment, the concentration of all olefins in the olefin composition is enriched by at least 50%, preferably by at least 75%, more preferably at least 90%. The concentration of the linear alpha olefin is enriched to at least 92%, preferably at least 96% by weight, of the total olefin concentration.

Fisher-Tropsch streams contain a variety of difficult to separate species, including saturated hydrocarbons, aromatics, oxygenates, internal olefins, branched olefins, and linear alpha olefins. An advantage of a Fisher-Tropsch stream is that it contains a mixture of both even and odd carbon, and the process of the invention produces a stream having even and odd carbon number olefin species at very low to zero amount of saturated hydrocarbons, with high concentrations of linear alpha olefins. The process of the invention can also provide a Fisher-Tropsch olefin composition having a mixture of internal olefins and/or branched olefins, and linear alpha olefins with low amounts of saturated hydrocarbons.

The process of the invention advantageously provides a linear alpha olefin stream that is highly concentrated in linear alpha olefins, wherein the concentration of linear alpha olefins in the linear alpha olefin composition may be at least 90%, preferably 96% linear alpha olefin purity in the linear alpha olefin composition.

The linear alpha olefin composition stream of the invention is useful as a component in drilling fluids, to react with elemental sulfur to make sulfurized products as extreme pressure agents in metal working fluids, as co-monomers for the polymerization of polyethylene, as an intermediate in making polyalpha olefins (PAO) used as a lubricant, as a chlorination feed to make polychlorinated hydrocarbons in PVC applications, to react with hydrogen sulfides to make primary and secondary mercaptans as pharmaceutical intermediates and as additives to modify the properties of rubber, as solvents, and as a precursor for the manufacture of plasticizer alcohols and detergent range alcohols and surfactants, which may be derivatized into detergent range sulfates or alkoxysulfates for laundry liquids and powders, dishwashing powders and liquids, bar soap, shampoo, liquid hand soap, and hard surface cleaners.

The ranges and limitations provided in the instant specification and claims are those that are believed to particularly point out and distinctly claim the instant invention. It is, however, understood that other ranges and limitations that perform substantially the same function in substantially the same manner to obtain the same or substantially the same result are intended to be within the scope of the instant invention. The present invention will now be illustrated by means of the following illustrative embodiments and examples that are provided for illustration and are not to be construed as limiting the invention.

The examples that follow are the predictions of plant simulation using AspenTech's Aspen10 Chemical Process Simulation Software. The important features of the process invention stem from the reaction equations described below and the kinetic rate constants tabulated below which were developed from reaction experiments.

All Reactions Follow the Kinetic Rate Expression $$r_{adduct} = k_f C_{olefin} C_{anthracene} - k_r C_{adduct}$$

Concentration units are gmol/liter. Rate constants have time units of inverse hours.

|  | $k_f$ | $k_r$ |
|---|---|---|
| 1-olefin | | |
| 250° C. | 0.51 | 0.07 |
| 280° C. | 1.63 | 0.72 |
| 310° C. | 4.60 | 6.51 |
| 2-methyl, 1-olefin | | |
| 250° C. | 0.11 | 0.25 |
| 280° C. | 0.48 | 3.38 |
| 310° C. | 1.77 | 37.05 |
| trans internal olefin | | |
| 250° C. | 0.11 | 0.04 |
| 280° C. | 0.48 | 0.57 |
| 310° C. | 1.77 | 6.30 |
| cis internal olefin | | |
| 250° C. | 0.11 | 0.65 |
| 280° C. | 0.48 | 7.81 |
| 310° C. | 1.77 | 76.14 |

EXAMPLE 1

A feedstock consisting of C9/C10 olefins, C9/C10 alkanes, and C7/C8 alcohols (see Table 1) is reacted with anthracene at a molar anthracene/olefin ratio of 2/1 in a plug flow reactor with 4.5 hr hold-up time. It leaves the reactor at 260° C. The alkanes, unreacted olefins, and alcohols are separated from the anthracene and adducts in two distillation stages. The anthracene/adducts stream is then fed to two continuous stirred tank reactors in series to crack the adduct. The olefin is taken off as vapor products and distilled to remove anthracene. The composition of the product is compared to the feedstock in Table 1.

TABLE 1

Without Re-equilibration Reactor

|  | Feedstock | Product |
|---|---|---|
| Composition (w %) | | |
| 1-olefin | 37.5 | 93.35 |
| 2-methyl-1-olefin | 4.5 | 2.82 |
| trans internal olefin | 3.0 | 3.82 |
| cis internal olefin | 3.0 | Trace |
| alkane | 47.0 | Trace |
| alcohol | 5.0 | Trace |
| Composition-Olefin only basis (w %) | | |
| 1-olefin | 78.12 | 95.36 |
| 2-methyl-1-olefin | 9.38 | 2.82 |
| trans internal olefin | 6.25 | 3.82 |
| cis internal olefin | 6.25 | Trace |
| Rate - lb/hr | 84,000 | 26,247 |

EXAMPLE 2

A feedstock consisting of C9/C10 olefins, C9/C10 alkanes, and C7/C8 alcohols (see Table 2) is reacted with anthracene at a molar anthracene/olefin ratio of 2/1 in a plug flow reactor with 4.5 hr hold-up time. It leaves the reactor at 260° C. The alkanes, unreacted olefins, and alcohols are partially separated from the anthracene and adducts using the first of two distillation stages. From the first distillation stage the anthracene/adduct rich bottoms product is then fed to a plug flow reactor for re-equilibration. Hold-up time for re-equilibration is ~0.8 hr. The re-equilibrator product leaves the reactor at 290° C. This product is then fed to the second distillation stage to remove all the alkanes, most of the free/unreacted olefins, and all the alcohol. The anthracene/adducts stream is then fed to two continuous stirred tank reactors in series to crack the adduct. The olefin is taken off as vapor products and distilled to remove anthracene. The composition of the product is compared to the feedstock in Table 2.

TABLE 2

With Re-equilibration Reactor

|  | Feedstock | Product |
|---|---|---|
| Composition (w %) | | |
| 1-olefin | 37.5 | 95.67 |
| 2-methyl-1-olefin | 4.5 | 0.89 |
| trans internal olefin | 3.0 | 3.42 |
| cis internal olefin | 3.0 | Trace |
| alkane | 47.0 | Trace |
| alcohol | 5.0 | Trace |
| Composition-Olefin only basis (w %) | | |
| 1-olefin | 78.12 | 95.69 |
| 2-methyl-1-olefin | 9.38 | 0.89 |
| trans internal olefin | 6.25 | 3.42 |
| cis internal olefin | 6.25 | Trace |
| Rate - lb/hr | 84,000 | 20,562 |

We claim:

1. A process for separating linear alpha olefins from a feedstock composition comprising linear alpha olefins, saturated hydrocarbons, internal olefins, branched olefins, and alcohol comprising:

a) contacting the feedstock composition with a linear polyaromatic compound under conditions effective to form a reaction mixture comprising linear polyaromatic compound-olefin adducts, saturated hydrocarbons, unreacted olefins, alcohols, and unreacted polyaromatic compound;

b) separating the linear polyaromatic compound-olefin adducts from the saturated hydrocarbons, unreacted olefins and alcohol in the reaction mixture to form a hydrocarbon stream comprising saturated hydrocarbons, unreacted olefins and alcohols and an adducted stream comprising the linear polyaromatic compound-olefin adducts and unreacted linear polyaromatic compound;

c) re-equilibrating the adducted stream by partially and selectively dissociating the linear polyaromatic compound-olefin adducts under conditions effective to increase the percentage of the polyaromatic compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound;

d) separating the linear polyaromatic compound-olefin adducts from the dissociated olefins in the equilibrated stream to form an olefin stream comprising dissociated olefins and a linear alpha-olefin adducted stream comprising the linear polyaromatic compound-olefin adducts and linear polyaromatic compound;

e) dissociating the linear polyaromatic compound-olefin adducts in the linear alpha olefin adducted stream to form linear polyaromatic compounds and alpha olefin enriched olefin product; and f) separating the alpha olefin enriched olefin product from the polyaromatic compounds, whereby the alpha olefin enriched olefin product is enriched in the concentration of olefins over the concentration of olefins in the feedstock and enriched in the concentration of linear alpha olefins over other olefins in the feedstock.

2. The process of claim 1 wherein the condition of step c) is carried out at a higher temperature than the condition of step a).

3. The process of claim 2 wherein in step c) the adducted stream is re-equilibrated by heating the adducted stream at a temperature in the range of from about 280° C. to about 310° C.

4. The process of claim 2 wherein the feedstock is contacted with a linear polyaromatic compound in step a) at a temperature in the range from about 200° C. to about 290° C.

5. The process of claim 4 wherein the feedstock is contacted with linear polyaromatic compound at a temperature ranging from about 220° C. to about 280° C.

6. The process of claim 2 wherein the molar ratio of olefins in the feedstock to linear polyaromatic compounds ranges from greater than 0.1:1 to 10:1.

7. The process of claim 1 wherein the linear polyaromatic compound-olefin adduct is dissociated by heating the linear polyaromatic compound-olefin adduct at a temperature in the range from about 250° C. to about 500° C.

8. The process of claim 7 wherein the linear polyaromatic compound-olefin adduct is heated in the dissociation step to a temperature in the range from about 300° C. to about 350° C.

9. The process of claim 1 wherein the linear polyaromatic compounds formed in step e) is separated from the alpha olefin enriched olefin product by vacuum or flash distillation.

10. The process of claim 1 wherein the separation in step b) is carried out by first cooling followed by filtration or centrifugation.

11. The process of claim 1 wherein the separation in step d) is carried out by first cooling followed by filtration or centrifugation.

12. The process of claim 1 wherein the feedstock comprises a stream derived from a Fisher-Tropsch process.

13. The process of claim 2 wherein the feedstock comprises a stream derived from a Fisher-Tropsch process.

14. The process of claim 12 wherein the feedstock comprises from 15 wt. % to 70 wt. % olefins, based on the weight of all ingredients in the feedstock.

15. The process of claim 14 wherein the feedstock comprises from 15 wt. % to 60 wt. % linear alpha olefins, based on the weight of all ingredients in the feedstock.

16. The process of claim 15 wherein the amount of all olefins in the feedstock other than linear alpha olefins ranges from 1 wt. % to 55 wt. %, based on the weight of all ingredients in the feedstock.

17. The process of claim 16 wherein the amount of all olefins other than linear alpha olefins in the feedstock ranges from 5 wt. % to 45 wt. %, based on the weight of all ingredients in the feedstock.

18. The process of claim 12 herein the feedstock comprises paraffins in an amount ranging from 5 wt. % to 99 wt. % based on the weight of all ingredients in the feedstock.

19. The process of claim 18 wherein the amount of paraffin ranges from 5 to 65 wt. % based on the weight of all ingredients in the feedstock.

20. The process of claim 18 wherein the amount of paraffin in the feedstock ranges from 65 wt. % to 99 wt. %.

21. The process of claim 1 wherein the feedstock comprises oxygenates and aromatics collectively present in the feedstock in an amount ranging from 5 wt. % to 30 wt. %, based on the weight of all ingredients in the feedstock.

22. The process of claim 1 wherein the feedstock has an average carbon number ranging from $C_5$–$C_{20}$ and wherein the predominant olefin species in the feedstock is within the range of $C_5$–$C_{20}$, inclusive.

23. The process of claim 1 wherein the alpha olefin enriched olefin product is at least 90 weight percent alpha olefin based on total olefins concentration.

24. The process of claim 23 wherein the alpha olefin enriched olefin product is at least 95 weight percent alpha olefin based on total olefins concentration.

25. The process of claim 23 wherein the alpha olefin enriched olefin product is at least 96 weight percent alpha olefin based on total olefins concentration.

26. The process of claim 13 wherein the feedstock comprises from 15 wt. % to 70 wt. % olefins, based on the weight of all ingredients in the feedstock.

27. The process of claim 26 wherein the feedstock comprises from 15 wt. % to 60 wt. % linear alpha olefins, based on the weight of all ingredients in the feedstock.

28. The process of claim 27 wherein the amount of all olefins in the feedstock other than linear alpha olefins ranges from 1 wt. % to 55 wt. %, based on the weight of all ingredients in the feedstock.

29. The process of claim 28 wherein the amount of all olefins other than linear alpha olefins in the feedstock ranges from 5 wt. % to 45 wt. %, based on the weight of all ingredients in the feedstock.

30. The process of claim 13 herein the feedstock comprises paraffins in an amount ranging from 5 wt. % to 99 wt. % based on the weight of all ingredients in the feedstock.

31. The process of claim 30 wherein the amount of paraffin ranges from 5 to 65 wt. % based on the weight of all ingredients in the feedstock.

32. The process of claim 30 wherein the amount of paraffin in the feedstock ranges from 65 wt. % to 99 wt. %.

33. A process for separating linear alpha olefins from a feedstock having an average carbon number in the range of from 5 to 20 and having a predominant olefin species within said range, said feedstock comprising olefins and saturated hydrocarbons and alcohols comprising;

a) contacting the feedstock composition with a linear polyaromatic compound under conditions effective to form a reaction mixture comprising linear polyaromatic compound-olefins adducts, saturated hydrocarbons, unreacted olefins, alcohols, and unreacted polyaromatic compound;

b) separating the linear polyaromatic compound-olefin adducts from the saturated hydrocarbons, unreacted olefins and alcohol in the reaction mixture to form a hydrocarbon stream comprising saturated hydrocarbons, unreacted olefins and alcohols and an adducted stream comprising the linear polyaromatic compound-olefin adducts and unreacted linear polyaromatic compound;

c) re-equilibrating the adducted stream by partially and selectively dissociating the linear polyaromatic compound-olefin adducts under conditions effective to increase the percentage of the polyaromatic compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound;

d) separating the linear polyaromatic compound-olefin adducts from the dissociated olefins in the equilibrated stream to form an olefin stream comprising dissociated olefins and a linear alpha-olefin adducted stream comprising the linear polyaromatic compound-olefin adducts and linear polyaromatic compound;

e) dissociating the linear polyaromatic compound-olefin adducts in the linear alpha olefin adducted stream to form linear polyaromatic compounds and alpha olefin enriched olefin product; and f) separating the alpha olefin enriched olefin product from the polyaromatic compounds, whereby the alpha olefin enriched olefin product is enriched in the concentration of olefins over the concentration of olefins in the feedstock and enriched in the concentration of linear alpha olefins over other olefins in the feedstock.

34. The process of claim 33 wherein the feedstock comprises a Fisher-Tropsch stream.

35. The process of claim 34 wherein the feedstock comprises from 15 wt. % to 60 wt. % linear alpha olefin, from 5 wt. % to 45 wt. % olefins other than linear alpha olefins, 5 wt. % to 99 wt. % paraffins, and 15 wt. % to 30 wt. % oxygenates and aromatics.

36. The process of claim 35, wherein the linear polyaromatic compound comprises anthracene or benzanthracene.

37. The process of claim 35 wherein the feedstock comprises linear alpha olefins, and the concentration of linear alpha olefins in the olefin composition is enriched by at least 40% over the concentration of linear alpha olefins present in the feedstock stream, and the concentration of saturated hydrocarbons in the olefin composition is reduced by at least 90% over the concentration of saturated hydrocarbons present in the feedstock.

38. The process of claim 33 wherein the condition of step c) is carried out at a higher temperature than the condition of step a).

39. The process of claim 38 wherein in step c) the adducted stream is re-equilibrated by heating the adducted stream at a temperature in the range of from about 280° C. to about 310° C.

40. The process of claim 39 wherein the feedstock is contacted with a linear polyaromatic compound in step a) at a temperature in the range from about 200° C. to about 290° C.

41. A process for separating linear alpha olefins from a Fisher-Tropsch feedstock having an average carbon number in the range of from 6 to 16 and having a predominant olefin species within said range, said feedstock comprising linear alpha olefins, olefins other than linear alpha olefins, saturated hydrocarbons, and alcohols comprising:

a) contacting said feedstock with a linear polyaromatic compound comprising anthracene or benzanthracene under conditions effective to form a reaction mixture comprising linear polyaromatic compound-olefin adducts, unreacted olefins, alcohols, saturated hydrocarbons, and unreacted polyaromatic compound;

b) separating the linear polyaromatic compound-olefin adducts from the saturated hydrocarbons, unreacted olefins and alcohol in the reaction mixture to form a hydrocarbon stream comprising saturated hydrocarbons, unreacted olefins, and alcohols, and an adducted stream comprising the linear polyaromatic compound-olefin adducts and unreacted linear polyaromatic compound;

c) re-equilibrating the adducted stream by partially and selectively dissociating the linear polyaromatic compound-olefin adducts under conditions effective to increase the percentage of the polyaromatic, compound reacted with linear alpha olefins over all other olefins reacted with the polyaromatic compound in the stream thereby producing a re-equilibrated stream comprising linear polyaromatic compound-olefin adducts, dissociated olefins, and unreacted and dissociated linear polyaromatic compound;

d) separating the linear polyaromatic compound-olefin adducts from the dissociated olefins in the equilibrated stream to form an olefin stream comprising dissociated olefins and a linear alpha-olefin adducted stream comprising the linear polyaromatic compound-olefin adducts and linear polyaromatic compound;

e) dissociating the linear polyaromatic compound-olefin adducts in the linear alpha olefin adducted stream to form linear polyaromatic compounds and alpha olefin enriched olefin product; and f) separating the alpha olefin enriched olefin product from the polyaromatic compound, whereby the alpha olefin enriched olefin product is enriched in the concentration of olefins over the concentration of olefins in the feedstock and enriched in the concentration of linear alpha olefins over other olefins in the feedstock.

42. The process of claim 41 wherein the condition of step c) is carried out at a higher temperature than the condition of step a).

43. The process of claim 42 wherein in step c) the adducted stream is re-equilibrated by heating the adducted stream at a temperature in the range of from about 280° C. to about 310° C.

44. The process of claim 43 wherein the feedstock is contacted with a linear polyaromatic compound in step a) at a temperature in the range from about 200° C. to about 290° C.

* * * * *